United States Patent
Sawada et al.

(10) Patent No.: US 8,859,109 B2
(45) Date of Patent: Oct. 14, 2014

(54) COMPOUND FOR ORGANIC ELECTROLUMINESCENT DEVICE AND ORGANIC ELECTROLUMINESCENT DEVICE USING THE SAME

(75) Inventors: Yuichi Sawada, Kitakyushu (JP); Takahiro Kai, Kitakyushu (JP); Masaki Komori, Kitakyushu (JP); Toshihiro Yamamoto, Kitakyushu (JP)

(73) Assignee: Nippon Steel & Sumikin Chemical Co., Ltd., Tokyo (JP)

( * ) Notice: Subject to any disclaimer, the term of this patent is extended or adjusted under 35 U.S.C. 154(b) by 341 days.

(21) Appl. No.: 12/934,078

(22) PCT Filed: Feb. 5, 2009

(86) PCT No.: PCT/JP2009/051973
§ 371 (c)(1),
(2), (4) Date: Sep. 23, 2010

(87) PCT Pub. No.: WO2009/119163
PCT Pub. Date: Oct. 1, 2009

(65) Prior Publication Data
US 2011/0024735 A1     Feb. 3, 2011

(30) Foreign Application Priority Data
Mar. 24, 2008  (JP) .................. 2008-075192

(51) Int. Cl.
*H01L 51/54* (2006.01)
*H01L 51/00* (2006.01)
(Continued)

(52) U.S. Cl.
CPC ............ *C07D 209/86* (2013.01); *H01L 51/006* (2013.01); *C09K 2211/1029* (2013.01); *H05B 33/14* (2013.01); *C09K 11/06* (2013.01); *C07D 401/14* (2013.01); *C07D 401/10* (2013.01); *C09K 2211/1007* (2013.01); *C09K 2211/1044* (2013.01); *C09K 2211/1011* (2013.01); *H01L 51/5048* (2013.01); *Y10S 428/917* (2013.01)

USPC ........... 428/690; 428/917; 313/504; 313/505; 313/506; 257/40; 257/E51.05; 257/E51.026; 257/E51.032; 548/304.1; 548/418; 548/440; 548/444

(58) Field of Classification Search
USPC ................. 428/690, 917; 313/504, 505, 506; 257/40, E51.05, E51.032, E51.026; 548/440, 418, 304.1, 444
See application file for complete search history.

(56) References Cited

U.S. PATENT DOCUMENTS

| 7,651,789 B2 | 1/2010 | Ogasawara et al. |
| 2002/0034655 A1 | 3/2002 | Watanabe et al. |

(Continued)

FOREIGN PATENT DOCUMENTS

| JP | 2001-313178 A | 11/2001 | |
| JP | 2003-031371 | * 1/2003 | ............. H05B 33/22 |

(Continued)

OTHER PUBLICATIONS

Hellwinkel et al., "Zur Frage des Pentakoodinierten Stickstoffs: Reaktion von (spiro)cyclischen Tetraarylammonium-Salzen mit Nucleophilen," Liebigs Ann. Chem. 762, 29-54 (1972).

(Continued)

*Primary Examiner* — Gregory Clark
(74) *Attorney, Agent, or Firm* — Birch, Stewart, Kolasch & Birch, LLP

(57) ABSTRACT

Disclosed is an organic electroluminescent device (organic EL device) that is improved in luminous efficiency, fully secured of driving stability, and of simple structure. The organic EL device comprises a light-emitting layer between an anode and a cathode piled one upon another on a substrate and the light-emitting layer comprises a phosphorescent dopant and a compound containing carbazolyl groups at both ends represented by the following formula (1) as a host material. In formula (1), X is independently CH optionally containing a substituent or N and L is a direct bond, an ethylene group, or an acetylene group.

3 Claims, 1 Drawing Sheet

(51) Int. Cl.
H05B 33/14 (2006.01)
C09K 11/06 (2006.01)
C07D 401/14 (2006.01)
C07D 401/10 (2006.01)
C07D 209/86 (2006.01)
H01L 51/50 (2006.01)

(56) References Cited

U.S. PATENT DOCUMENTS

2005/0287393 A1   12/2005   Lee et al.
2006/0186796 A1*  8/2006    Yabe et al. .................... 313/504
2007/0196692 A1   8/2007    Ise et al.
2009/0236973 A1*  9/2009    Yabe et al. .................... 313/504

FOREIGN PATENT DOCUMENTS

| JP | 2003-515897 T | 5/2003 |
| JP | 2004-273190 A | 9/2004 |
| JP | 2005-259412 A | 9/2005 |
| JP | 2006-13482 A | 1/2006 |
| JP | 2006-156445 * | 6/2006 ............. H01L 51/50 |
| JP | 2006-199679 A | 8/2006 |
| JP | 2006-232813 A | 9/2006 |
| JP | 2007-67383 A | 3/2007 |
| JP | 2007-227658 A | 9/2007 |

OTHER PUBLICATIONS

Holmes et al., "Blue organic electrophosphorescence using exothermic host-guest energy transfer," Applied Physics Letters, vol. 82, No. 15, Apr. 14, 2003, pp. 2422-2424.
Tao et al., "A Simple Carbazole/Oxadiazole Hybrid Molecule: An Excellent Bipolar Host for Green and Red Phosphorescent OLEDs," Agnew. Chem. Int. Ed. 2008, 47, 8104-8107.
Tokito et al., "Confinement of triplet energy on phosphorescent molecules for highly-efficient organic blue-light-emitting devices," Applied Physics Letters, vol. 83, No. 3, Jul. 27, 2003, pp. 569-571.
English language translation of the International Preliminary Report on Patentability dated Feb. 9, 2010 for Application No. PCT/JP2009/051973 (PCT/IPEA/409).

* cited by examiner

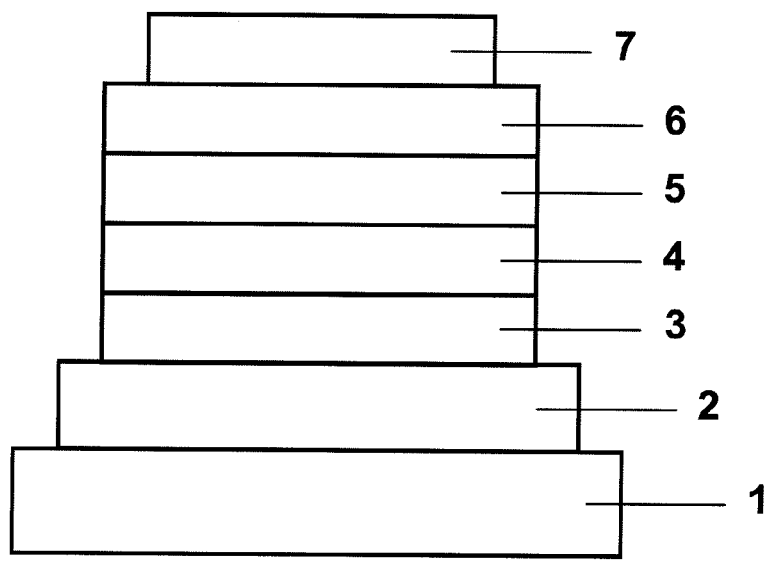

COMPOUND FOR ORGANIC ELECTROLUMINESCENT DEVICE AND ORGANIC ELECTROLUMINESCENT DEVICE USING THE SAME

FIELD OF TECHNOLOGY

This invention relates to a compound for organic electroluminescent device and an organic electroluminescent device using the same and, more particularly, this invention relates to a thin film type device that emits light by application of an electrical field to a light-emitting layer composed of an organic compound.

BACKGROUND TECHNOLOGY

An organic electroluminescent device (hereinafter referred to as organic EL device) in the simplest structure is generally constituted of a light-emitting layer sandwiched between a pair of counter electrodes and functions by utilizing the following phenomenon. Upon application of an electrical field between the electrodes, electrons are injected from the cathode and holes are injected from the anode and they recombine in the light-emitting layer with emission of light.

In recent years, organic thin films have been used in the development of organic EL devices. In particular, in order to enhance the luminous efficiency, the kind of electrodes has been optimized for the purpose of improving the efficiency of injecting carriers from the electrodes and a device has been developed in which a hole-transporting layer composed of an aromatic diamine and a light-emitting layer composed of 8-hydroxyquinoline aluminum complex (hereinafter referred to as Alq3) are disposed in thin film between the electrodes. This device has brought about a marked improvement in the luminous efficiency over the conventional devices utilizing single crystals of anthracene and the like and thereafter the developmental works of organic EL devices have been focused on commercial applications to high-performance flat panels featuring self-luminescence and high-speed response.

In another effort to enhance the luminous efficiency of the device, the use of phosphorescence in place of fluorescence is investigated. The aforementioned device comprising a hole-transporting layer composed of an aromatic diamine and a light-emitting layer composed of Alq3 and many other devices utilize fluorescence. The use of phosphorescence, that is, emission of light from the excited triplet state, is expected to enhance the luminous efficiency three to four times that of the conventional devices utilizing fluorescence (emission of light from the excited singlet state). To achieve this objective, the use of coumarin derivatives and benzophenone derivatives in the light-emitting layer was investigated, but these derivatives merely produced luminance at an extremely low level. Thereafter, europium complexes were tried to utilize the excited triplet state, but failed to emit light at high efficiency. In recent years, as is mentioned in patent document 1, a large number of researches are conducted with the objective of enhancing the luminous efficiency and extending the life while giving priority to utilization of organic metal complexes such as iridium complexes.

Patent document 1: JP2003-515897 A
Patent document 2: JP2001-313178 A
Patent document 3: JP2004-273190 A
Patent document 4: JP2005-259412 A
Patent document 5: JP2006-199679 A
Patent document 6: JP2007-227658 A
Non-patent document 1: Applied Physics Letters, 2003, 83, 569-571
Non-patent document 2: Applied Physics Letters, 2003, 82, 2422-2424

In order to enhance the luminous efficiency, a host material to be used together with the dopant material becomes important. Of the host materials proposed thus far, a typical example is 4,4'-bis(9-carbazolyl)biphenyl (hereinafter referred to as CBP), which is a carbazole compound presented in patent document 2. When used as a host material for green phosphorescent emitters, typically tris(2-phenylpyridine)iridium complex (hereinafter referred to as Ir(ppy)3), CBP exhibits relatively good luminous characteristics. On the other hand, CBP fails to perform at sufficiently high luminous efficiency when used as a host material for common blue phosphorescent emitters. This is because the lowest triplet energy level of CBP is lower than that of common blue phosphorescent emitters and the triplet energy of a blue phosphorescent emitter is transferred to CBP. That is to say, if a phosphorescent host material were designed to have triplet energy higher than that of a phosphorescent emitter, the triplet energy of the said phosphorescent emitter would be confined effectively and, as a result, the luminous efficiency would be enhanced. With the objective of improving the energy-confining effect, the structure of CBP is modified to increase the triplet energy thereby enhancing the luminous efficiency of iridium bis[2-(4,6-difluorophenyl)pyridinato-N,C2']picolinate (hereinafter referred to as FIrpic) in non-patent document 1. Similarly, the luminous efficiency is enhanced by using 1,3-dicarbazolylbenzene (hereinafter referred to as mCP) as a host material in non-patent document 2. However, these host materials are not satisfactory in practical use, particularly from the viewpoint of durability.

Moreover, the host material needs to have well-balanced electrical charges (hole and electron) injection/transport characteristics in order to enhance the luminous efficiency. The electron transport property falls short of the hole transport property in the case of CBP and this disturbs the balance of electrical charges in the light-emitting layer and causes excess holes to flow out to the cathode side thereby reducing the probability of recombination of holes and electrons in the light-emitting layer and lowering the luminous efficiency. Furthermore, the recombination in this case occurs in a narrow limited region in the vicinity of the interface on the cathode side. Therefore, in the case where an electron-transporting material like Alq3 whose lowest triplet energy level is lower than that of Ir(ppy)3 is used, there may also arise the possibility that the luminous efficiency may become lower due to transfer of the triplet energy from the dopant to the electron-transporting material.

One of the means to prevent holes from flowing out to the electron-transporting layer is to provide a hole-blocking layer between the light-emitting layer and the electron-transporting layer. The hole-blocking layer accumulates holes efficiently in the light-emitting layer and contributes to improvement of the probability of recombination of holes and electrons in the light-emitting layer and enhancement of the luminous efficiency (patent document 2). The hole-blocking materials in general use include 2,9-dimethyl-4,7-diphenyl-1,10-phenanthroline (hereinafter referred to as BCP) and p-phenylphenolato-bis(2-methyl-8-quinolinolato)aluminum (hereinafter referred to as BAlq). These materials can prevent holes from flowing out of the light-emitting layer to the electron-transporting layer; however, the lowest triplet energy level of both of them is low compared with that of a phosphorescent dopant such as Ir(ppy)3 and sufficient luminous efficiency cannot be obtained.

Moreover, BCP tends to crystallize even at room temperature and lacks reliability as a hole-blocking material and the life of the device is extremely short. Although BAlq is reported to have a Tg of approximately 100° C. and provide the device with relatively good life, its hole-blocking ability is not enough. In addition, there arises a problem that an increment of one layer complicates the structure of the device and increases the production cost.

As described above, in order for an organic EL device to perform at high luminous efficiency, a host material is required to have high triplet energy and to be balanced in the electrical charges (hole and electron) injection/transport characteristics. Furthermore, the host material is desirably a compound endowed with electrochemical stability, high heat resistance, and excellent stability in the amorphous state. However, no compound capable of satisfying these properties on a practical level is known at the present time Some of the organic EL devices developed so far by making use of phosphorescent molecules use materials containing a carbazole ring (carbazole skeleton) as host materials in the light-emitting layer. In recent years, several materials containing a carbazole ring have been proposed for the purpose of increasing the triplet energy.

A biphenyl derivative containing carbazole rings shown below is proposed as a host material in patent document 3.

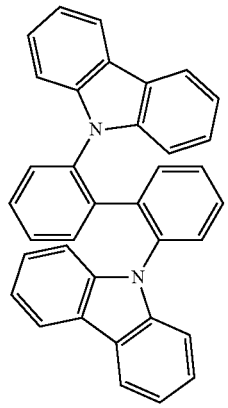 [SMILES: c1ccc(-n2c3ccccc3c3ccccc32)c(-c2ccccc2-n2c3ccccc3c3ccccc32)c1]

In the aforementioned compound, the carbazole rings are linked to the aromatic ring of biphenyl skeleton and this configuration causes the electron transport property to fall short of the hole transport property in the molecule. Hence, the electrical charges are balanced poorly and the durability is insufficient. Furthermore, when attention is paid to two benzene rings in the aforementioned biphenyl skeleton, each of them is linked to the carbazole ring at the ortho position and this configuration develops a strain in the molecule and causes a loss of stability thereby emphasizing all the more the aforementioned problem.

The following compound and others are shown as luminous materials in patent document 4.

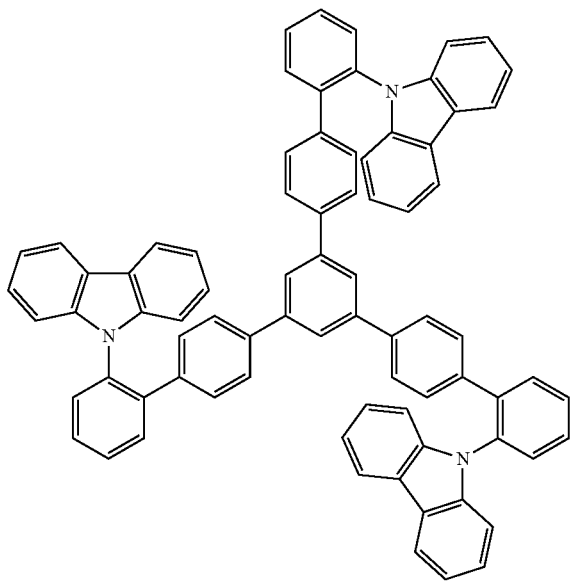 [SMILES: c1ccc(-n2c3ccccc3c3ccccc32)c(-c2ccc(-c3cc(-c4ccc(-c5ccccc5-n5c6ccccc6c6ccccc65)cc4)cc(-c4ccc(-c5ccccc5-n5c6ccccc6c6ccccc65)cc4)c3)cc2)c1]

However, in the aforementioned compound, the benzene ring at the center is trivalent and linked to three 5'-carbazolyl-biphenyl groups like a starburst structure. Hence, it is likely that the triplet energy becomes lower and sufficient luminous efficiency cannot be obtained.

Further, the following compounds are proposed as luminous materials in patent document 5.

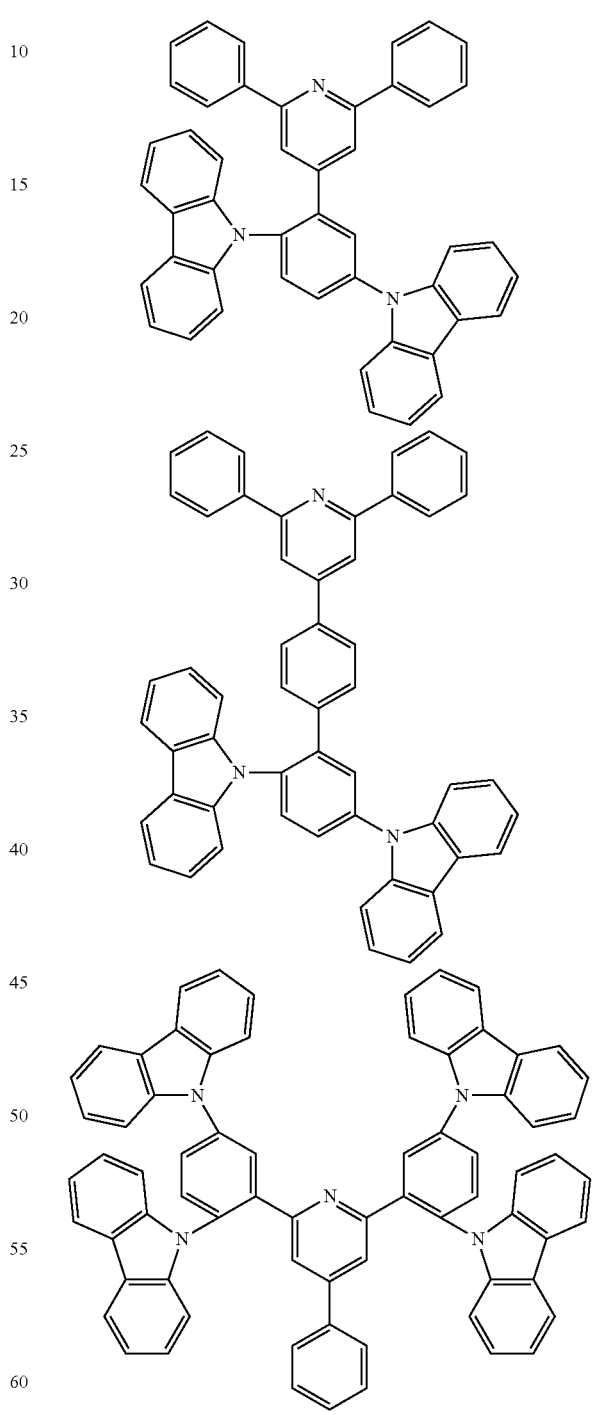

However, in the aforementioned compounds, one benzene ring is substituted with two carbazolyl groups and, when the compounds are subjected to electrical oxidation/reduction, it is conceivable that localization of electrical charges between the carbazole ring responsible for the hole transport property and the benzene ring responsible for the electron transport property becomes extensive and the result is a lack of electrical stability.

The following compound is shown as a luminous material in patent document 6.

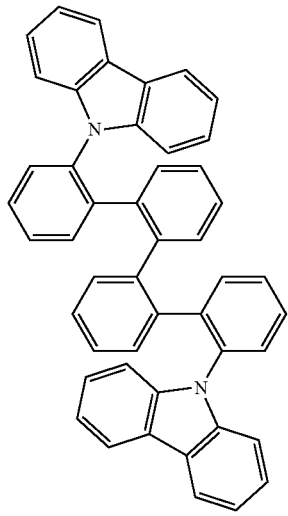 [SMILES: c1ccc(-c2ccccc2-n2c3ccccc3c3ccccc32)c(-c2ccccc2-c2ccccc2-n2c3ccccc3c3ccccc32)c1]

However, the aforementioned compound possesses two terminal carbazolylphenyl groups respectively substituted at the ortho position. Hence, the compound has high triplet energy and the luminous efficiency is enhanced. However, a large strain develops in the molecule when all the benzene rings are linked to one another at the ortho position as in the aforementioned compound; in such a case, charge delocalization becomes difficult to occur between the aromatic rings when the compound is subjected to electrical oxidation/reduction, an excessive load is imposed on the molecule, and the durability becomes insufficient.

DISCLOSURE OF THE INVENTION

Problems to be Solved by the Invention

In applications of organic EL devices to display devices such as flat panel displays, it is necessary to enhance the luminous efficiency of the device and, at the same time, to fully secure the driving stability of the device. Under the aforementioned circumstances, an object of this invention is to provide an organic EL device of high efficiency, good driving stability, and practical usefulness and to provide a compound suitable therefor.

Means to Solve the Problems

The inventors of this invention have found as a result of intensive studies that a compound that is terminated at both ends with a partial structure made up of a carbazolyl group linked to a six-membered aromatic ring at the ortho position is suitable as a compound for an organic EL device and completed this invention.

Accordingly, this invention relates to a compound for organic electroluminescent device represented by the following general formula (1).

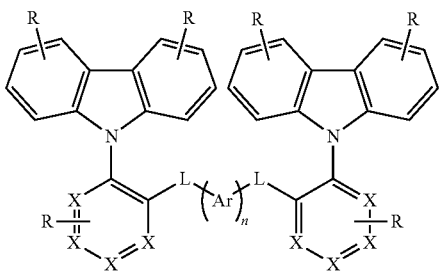

In general formula (1), Ar is a divalent aromatic hydrocarbon group of 6-18 carbon atoms optionally containing substituents or a divalent aromatic heterocyclic group of 3-18 carbon atoms optionally containing substituents and n Ars are identical with or different from one another; L is a direct bond, an ethylene group, or an acetylene group; X is independently a methine group optionally containing a substituent or a nitrogen atom; Rs each is independently a hydrogen atom, an alkyl group of 1-6 carbon atoms, an alkoxyl group of 1-6 carbon atoms, an acyl group of 1-6 carbon atoms, an aromatic hydrocarbon group of 6-18 carbon atoms optionally containing substituents, or an aromatic heterocyclic group of 3-18 carbon atoms optionally containing substituents; n is an integer of 1-3; in the case where L is a direct bond, not all the bonds between L and Ar and between n Ars are located at the adjacent position in the aromatic rings constituting Ars.

Of the compounds represented by the aforementioned general formula (1), compounds represented by the following general formula (2) are preferred.

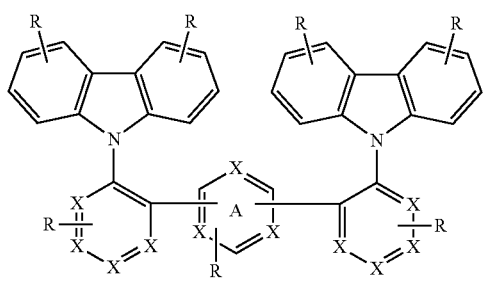

In general formula (2), n, X, and R respectively have the same meaning as n, X, and R in general formula (1); in at least one of n (ring A)s, two bonds linking the adjacent rings are not located at the ortho position.

This invention also relates to an organic electroluminescent device comprising an anode, organic layers, and a cathode piled one upon another on a substrate wherein the device comprises an organic layer comprising the aforementioned compound for organic electroluminescent device.

Further, this invention assumes the following desirable forms.
1) The aforementioned compound for organic electroluminescent device wherein, in general formula (1), Ar is a substituted or unsubstituted aromatic hydrocarbon group of 6-18 carbon atoms or a substituted or unsubstituted aromatic heterocyclic group of 3-18 carbon atoms.
2) The aforementioned compound for organic electroluminescent device wherein, in general formula (1), X is a methine group.
3) The aforementioned compound for organic electroluminescent device wherein, in general formula (1), L is a direct bond.

4) The aforementioned compound for organic electroluminescent device wherein, in general formula (1), R is a hydrogen atom.
5) The aforementioned organic electroluminescent device comprising an anode, organic layers, and a cathode piled one upon another on a substrate wherein the organic layer comprising the aforementioned compound for organic electroluminescent device is at least one layer selected from the group of a light-emitting layer, a hole-transporting layer, an electron-transporting layer, and a hole-blocking layer.
6) The aforementioned organic electroluminescent device wherein the organic layer comprising the aforementioned compound for organic electroluminescent device is a light-emitting layer further comprising a phosphorescent dopant.

BRIEF DESCRIPTION OF THE DRAWING

FIG. 1 schematically shows the cross section of an example of an organic EL device.

PREFERRED EMBODIMENTS OF THE INVENTION

A compound for organic EL device according to this invention is represented by the aforementioned general formula (1).

In general formula (1), Ar is a divalent aromatic hydrocarbon group of 6-18 carbon atoms or a divalent aromatic heterocyclic group of 3-18 carbon atoms. The divalent aromatic hydrocarbon group or aromatic heterocyclic group may contain substituents. Further, n Ars may be identical with or different from one another. The term "an aromatic hydrocarbon group optionally containing substituents" as used in this specification means both an aromatic hydrocarbon group containing no substituent and an aromatic hydrocarbon group containing substituents. The same holds for an aromatic heterocyclic group optionally containing substituents, and a methine group optionally containing a substituent.

Examples of the preferable divalent aromatic hydrocarbon groups include the groups formed by removing two hydrogen atoms from aromatic hydrocarbons of single-ring or fused-ring structure such as benzene, naphthalene, phenanthrene, anthracene, and fluorene. A phenylene group and a naphthylene group are preferred. When n is 2 and two Ars are phenylene groups in general formula (1), —(Ar)$_n$— becomes a biphenylylene group.

Examples of the preferable divalent aromatic heterocyclic groups include the groups formed by removing two hydrogen atoms from aromatic heterocyclic compounds such as furan, pyran, pyrrole, imidazole, pyrazole, isothiazole, isoxazole, pyridine, pyrazine, pyrimidine, pyridazine, thianthrene, isobenzofuran, chromene, xanthene, phenoxanthene, indolizine, isoindole, indazole, purine, quinoline, isoquinoline, naphthyridine, quinoxaline, quinazoline, carbazole, phenathrine, acridine, perimidine, phenazine, phenothiazine, phenoxazine, thiazole, oxazole, dibenzodioxin, triazole, benzoxazole, benzothiazole, benzimidazole, and benzotriazole. The groups formed by removing two hydrogen atoms from pyridine, pyrimidine, pyrazine, triazine, and carbazole are preferred.

The aforementioned aromatic hydrocarbon groups and aromatic heterocyclic groups may contain substituents. Examples of preferable substituents include an alkyl group, an aromatic hydrocarbon group, an acyl group, an alkoxyl group, an aryloxy group, an alkylthio group, an arylthio group, an alkoxycarbonyl group, an aryloxycarbonyl group, a halogen atom, an arylamino group, an alkylamino group, and an aromatic heterocyclic group. From the viewpoint of obtaining a high triplet energy level and avoiding a lowering of electrical durability accompanying a maldistribution of electrical charges, a phenyl group, a pyridyl group, and an alkyl group of 1-4 carbon atoms are preferred. In the case where the aforementioned substituents can contain two or more carbon atoms, the number of carbon atoms is 18 or less, preferably 10 or less. In the case where the substituents are aromatic hydrocarbon groups or the like, they may further contain substituents such as halogen atoms.

In general formula (1), L is a direct bond, an ethylene group, or an acetylene group. A direct bond or an ethylene group is preferred.

In general formula (1), Rs each is independently a hydrogen atom, an alkyl group of 1-6 carbon atoms, an alkoxyl group of 1-6 carbon atoms, an acyl group of 1-6 carbon atoms, an aromatic hydrocarbon group of 6-18 carbon atoms optionally containing substituents, or an aromatic heterocyclic group of 3-18 carbon atoms optionally containing substituents. From the viewpoint of obtaining a high triplet energy level and avoiding a lowering of electrical durability accompanying a maldistribution of electrical charges, a hydrogen atom, an alkyl group of 1-6 carbon atoms, a phenyl group optionally containing substituents, or a pyridyl group optionally containing substituents is preferred. In the case of aromatic hydrocarbon groups optionally containing substituents or aromatic heterocyclic groups optionally containing substituents, the said substituents may be the same as the aforementioned substituents.

In general formula (1), X is independently a methine group optionally containing a substituent or a nitrogen atom. Of the 4 Xs in the six-membered ring, 3 or more, preferably 4, are methine groups and the rest is a nitrogen atom.

In the case of a methine group optionally containing a substituent, examples of the substituent include an alkyl group of 1-6 carbon atoms, an alkoxyl group of 1-6 carbon atoms, an acyl group of 1-6 carbon atoms, an aromatic hydrocarbon group of 6-18 carbon atoms, and an aromatic heterocyclic group of 3-18 carbon atoms.

In general formula (1), n is an integer of 1-3, preferably 1. In the case where n is 2 or 3, n Ars may be identical with or different from one another.

In the case where L is a direct bond in general formula (1), not all the bonds between L and Ar and between n Ars are located at the adjacent position in the aromatic rings constituting Ars and they are at least partly located at the position other than the adjacent position. That is, supposing n Ars are designated as Ar1, Ar2, and Ar3, they are linked something like -L-Ar1-Ar2-Ar3-L- in general formula (1). When attention is paid to Ar1, the position at which L is linked to Ar1 and the position at which Ar1 is linked to Ar2 happen to be adjacent to each other (or at the ortho position in the case of a six-membered ring) in some cases. Likewise, when attention is paid to Ar2, the position at which Ar2 is linked to Ar1 and the position at which Ar2 is linked to Ar3 happen to be adjacent to each other in some cases. And, two bonds linking the adjacent Ars are located at the adjacent position not in all of n Ars in general formula (1). In the case where n is 2 or 3, it suffices that the aforementioned two bonds are not located at the adjacent position in one of Ars and the position of two bonds may be arbitrary in the remaining Ar or Ars; however, the aforementioned two bonds are preferably not located at the adjacent position in all of n Ars. In the case where L is not a direct bond, the restriction of this kind is not essential; however, the aforementioned two bonds are preferably not located at the adjacent position in one of Ars.

The compounds preferable for this invention are those represented by the aforementioned general formula (2). In general formula (2), n, X, and R respectively have the same meaning as n, X, and R in general formula (1). It is to be understood that Ar in general formula (1) corresponds to ring A in general formula (2) and L is a direct bond in general formula (2).

Ring A in general formula (2) corresponds to Ar in general formula (1) and it is a six-membered aromatic ring in which the atoms constituting the ring are limited to carbon and X. Here, X in ring A has the same meaning as X in the ring linked to the N-carbazolyl group (N-linked ring), but it can vary independently. The nature of preferred ring A can be understood by selecting a six-membered aromatic group whose ring is made up of carbon atoms and X from the aromatic groups regarded as desirable in the aforementioned explanation of Ar.

In general formula (2), two bonds linking the adjacent rings are located at the ortho position not in all of n (ring A)s. The explanation given on the bonding position of n Ars in general formula (1) applies here and this configuration is designed to prevent deterioration of the stability and durability and reduction of the life of the compound that may occur when all the adjacent rings are linked at the adjacent position or the ortho position.

The compounds of this invention represented by general formula (1) or (2) can be synthesized by selecting raw materials to suit the structure of the target compound and utilizing a known procedure.

Several methods are available for the synthesis; for example, one method consists of synthesizing a compound having a skeleton of aromatic chain to be linked later to two carbazole rings and introducing the carbazole groups in the final stage (method 1) while another method consists of coupling an o-carbazolylarylboronic acid and an aryl halide whose skeleton corresponds to L-(Ar)$_n$-L in general formula (1) (method 2).

According to method 1, a compound containing halogen atoms as substituents in its basic skeleton and substituted or unsubstituted carbazole are mixed with a strong base such as sodium hydride, potassium tert-butoxide, and n-butyllithium in a solvent such as tetrahydrofuran, dioxane, diethyl ether, and N,N-dimethylformamide and heated under reflux with stirring in an atmosphere of dry gas and/or inert gas.

According to method 2, an o-carbazolylarylboronic acid is allowed to react with an aryl halide in a solvent in the presence of a metal catalyst and a base.

Examples of the compounds represented by general formula (1) are shown below, but the compounds for organic El devices of this invention are not limited to these examples.

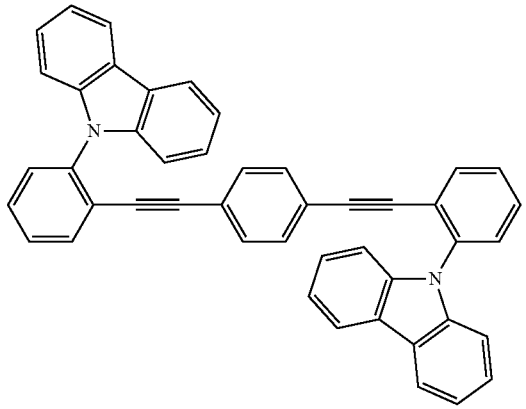

1

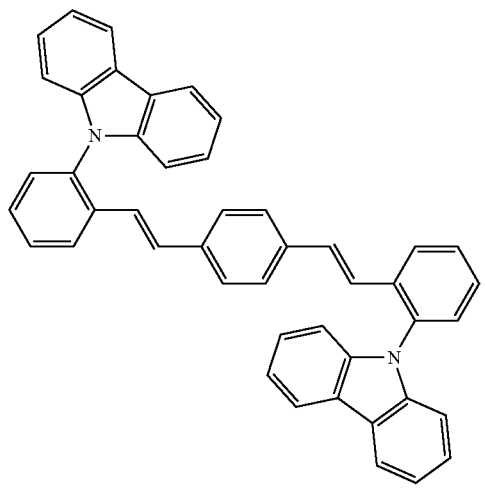

2

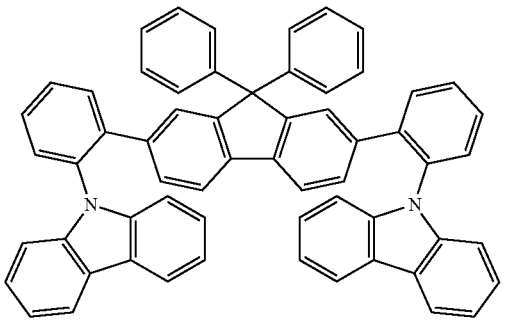

3

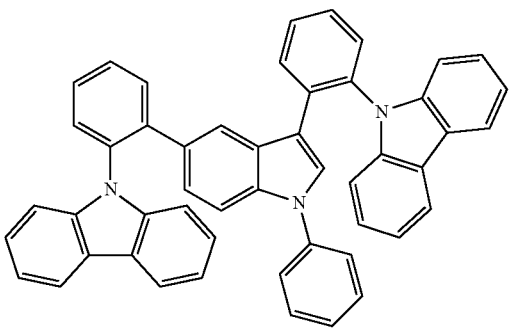

4

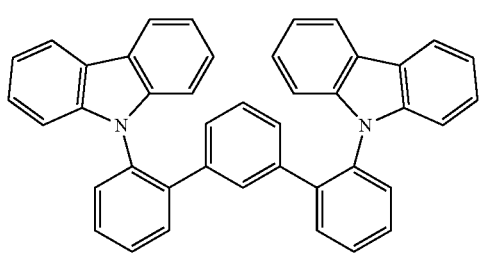

5

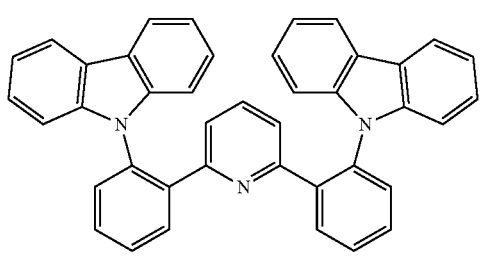

6

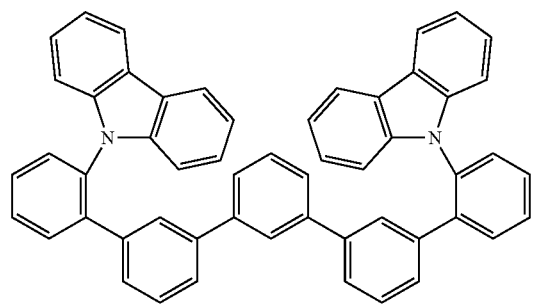
7
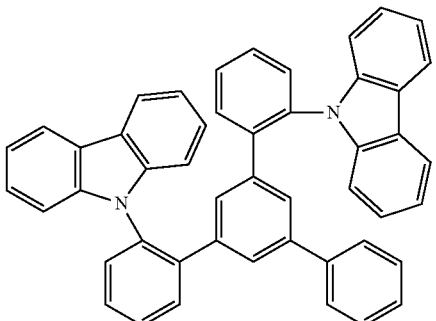
12
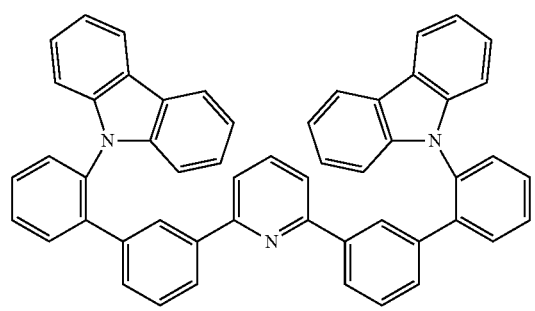
8
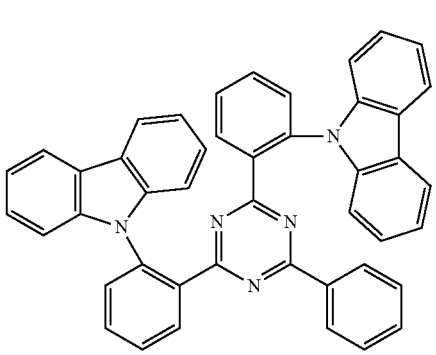
13
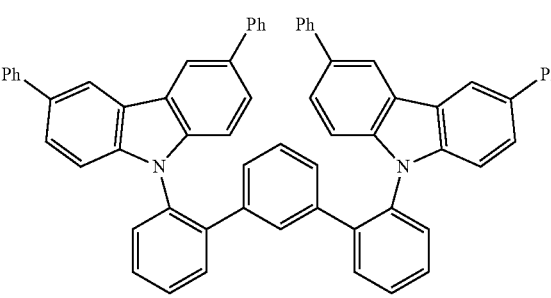
9
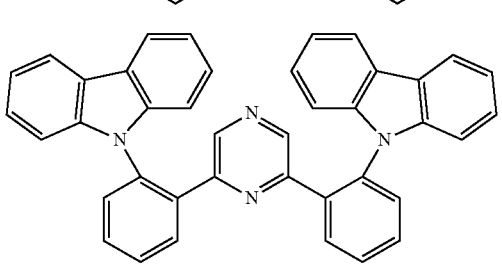
14
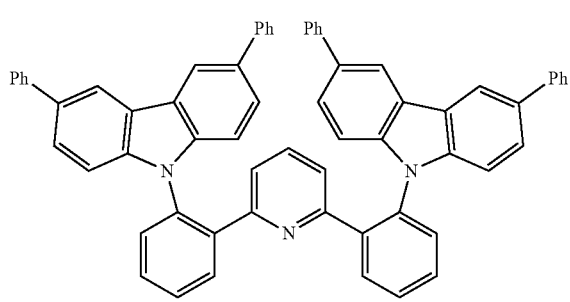
10
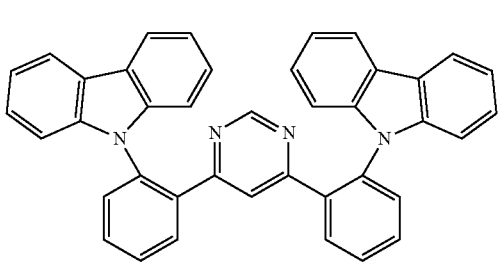
15
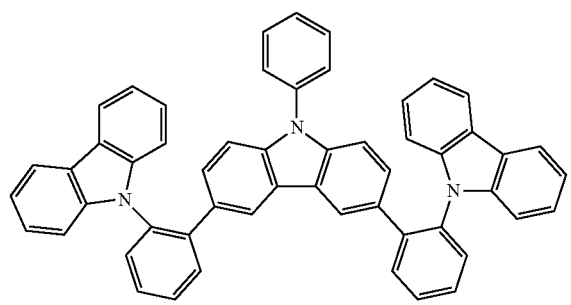
11
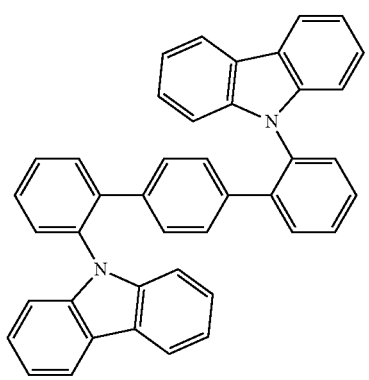
16

17
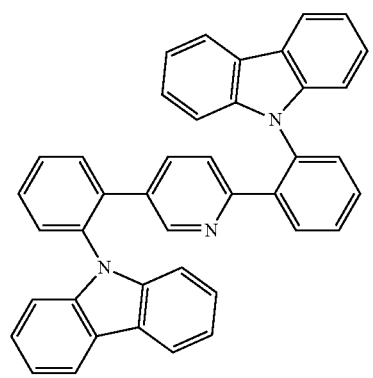
18
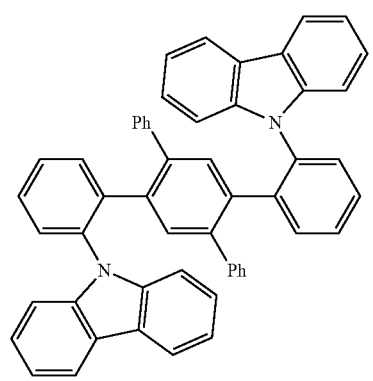
19
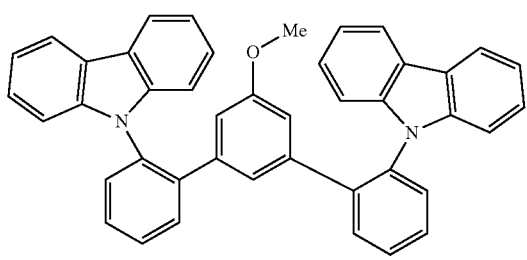
20
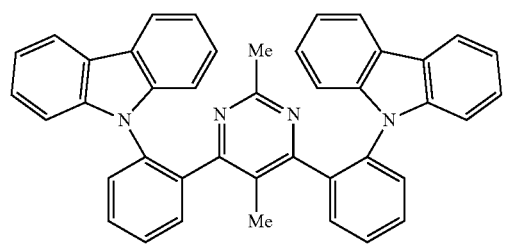
21
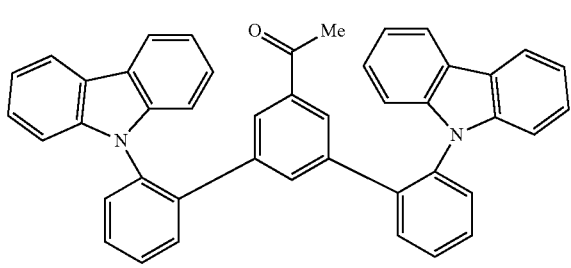
22
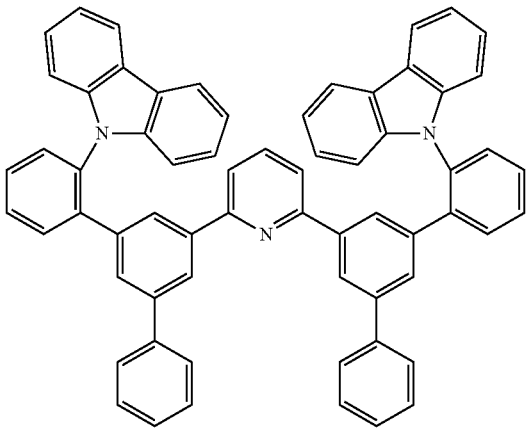
23
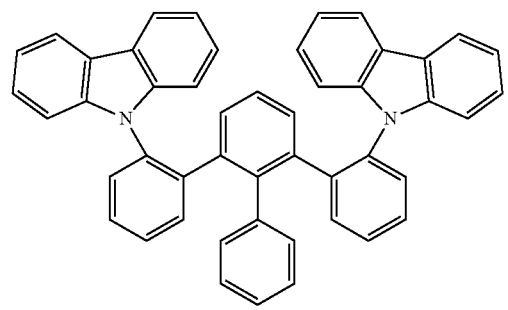
24
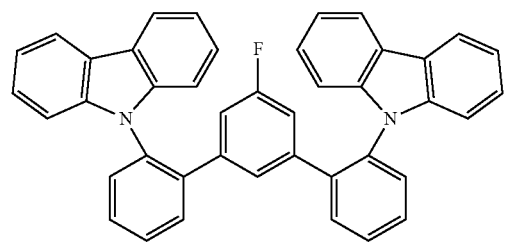
25
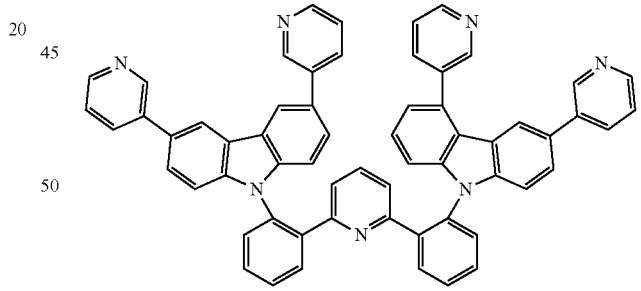
26
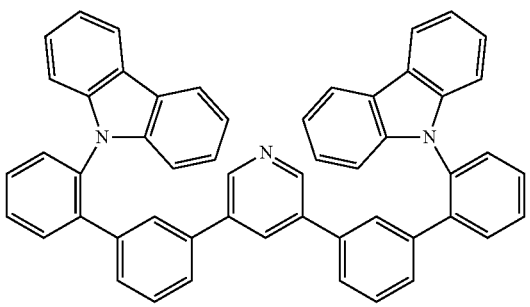

The compound for organic electroluminescent device of this invention provides an organic EL device of excellent quality when incorporated in an organic layer of an organic EL device comprising an anode, organic layers, and a cathode piled one upon another on a substrate. The organic layer suitable for incorporation of the compound is a light-emitting layer, a hole-transporting layer, an electron-transporting layer, or a hole-blocking layer. Incorporation of the compound in the light-emitting layer is preferred and incorporation of the compound as a host material in the light-emitting layer containing a phosphorescent dopant is more preferred.

The materials for phosphorescent dopants to be used in the light-emitting layer are preferably organic metal complexes containing at least one metal selected from ruthenium, rhodium, palladium, silver, rhenium, osmium, iridium, platinum, and gold. Such organic metal complexes are known in the aforementioned patent documents and elsewhere and a suitable complex can be selected from them and used in this invention.

Preferable phosphorescent dopants include complexes having a noble metal element such as Ir in the center, typically Ir(ppy)3, complexes such as Ir(bt)2.acac3, and complexes such as PtOEt3. Examples of these complexes are shown below, but are not limited thereto.

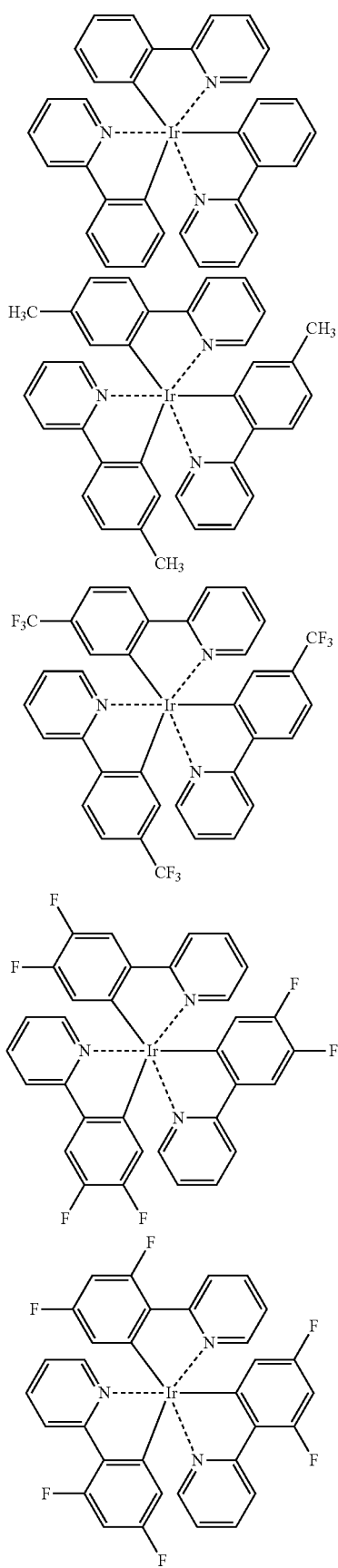
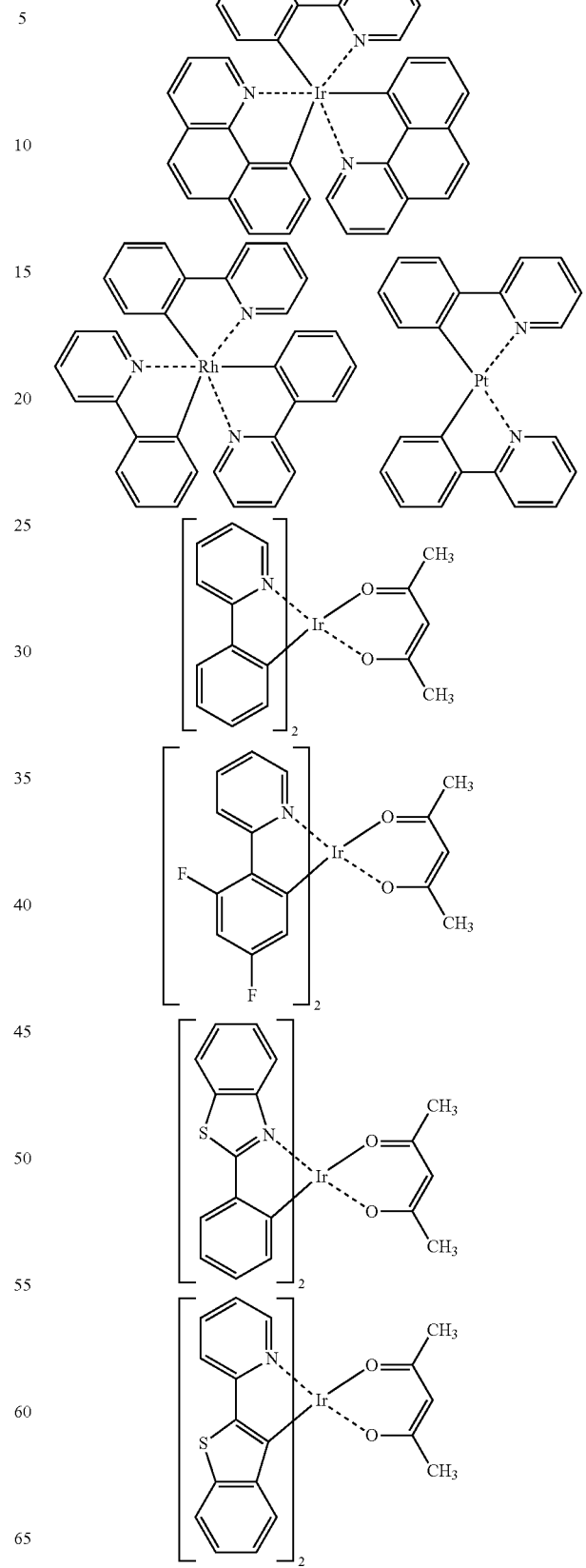

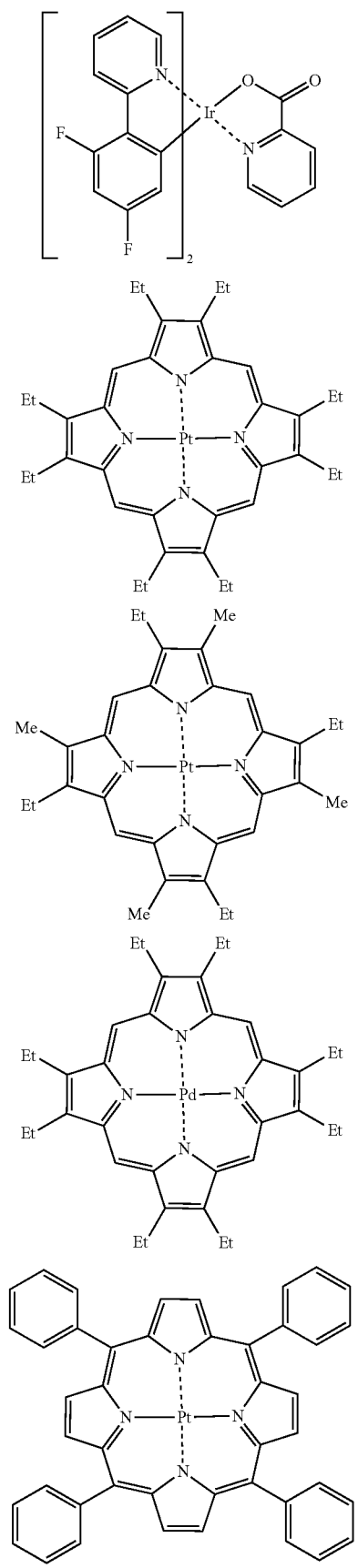
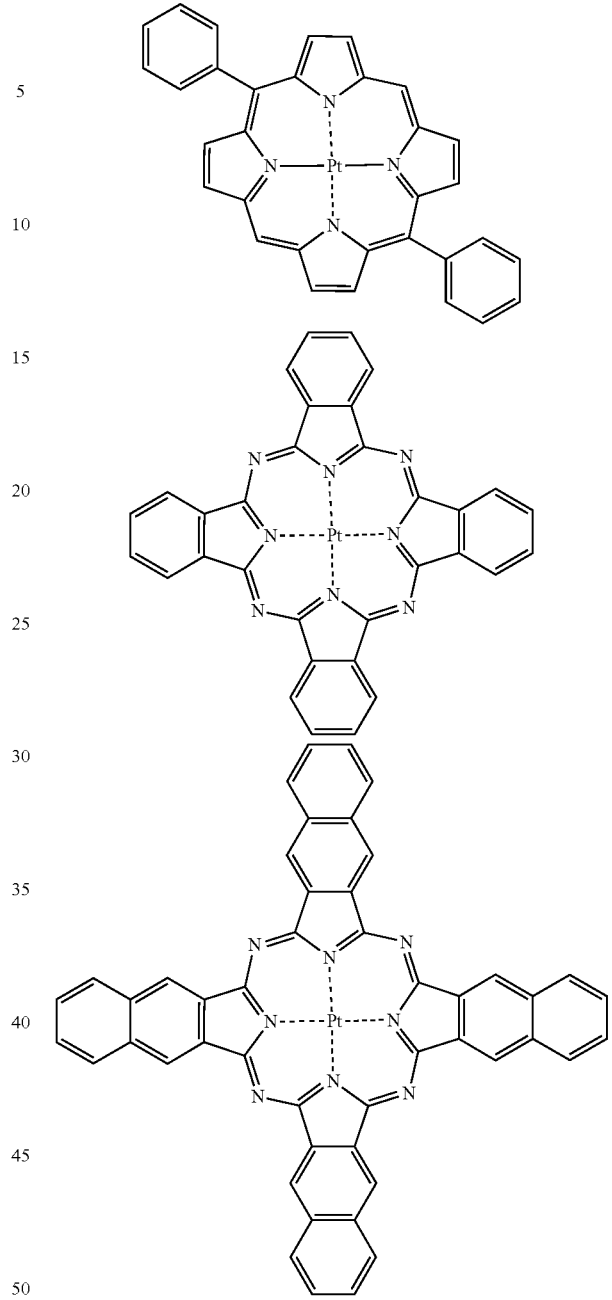

The content of the aforementioned phosphorescent dopant in the light-emitting layer is preferably in the range of 5-10 wt %.

The organic EL device in which the compound for organic EL device of this invention is used will be explained next. The organic EL device of this invention comprises organic layers between an anode and a cathode piled one upon another on a substrate and at least one of the organic layers is a light-emitting layer and at least one layer comprises the compound for organic EL device of this invention. Advantageously, the light-emitting layer comprises the compound for organic EL device of this invention. More advantageously, the light-emitting layer comprises the compound for organic EL device of this invention together with a phosphorescent dopant.

The structure of the organic EL device of this invention will be explained with reference to the drawing, but it will not be limited to the one illustrated in the drawing.

Explanation of symbols: 1 substrate, 2 anode, 3 hole-injecting layer, 4 hole-transporting layer, 5 light-emitting layer, 6 electron-transporting layer, 7 cathode.

FIG. 1 schematically shows the structure of an example of an organic EL device generally used in this invention and the numbers respectively stand for the following; 1 for a substrate, 2 for an anode, 3 for a hole-injecting layer, 4 for a hole-transporting layer, 5 for a light-emitting layer, 6 for an electron-transporting layer, and 7 for a cathode. The organic EL device of this invention comprises a substrate, an anode, a light-emitting layer, and a cathode as essential layers; in addition to these essential layers, the device preferably has a hole-injecting/transporting layer and an electron-injecting/transporting layer and, further, has a hole-blocking layer disposed between the light-emitting layer and the electron-injecting/transporting layer. The term hole-injecting/transporting layer means a hole-injecting layer and/or a hole-transporting layer and the term electron-injecting/transporting layer means an electron-injecting layer and/or an electron-transporting layer.

It is possible to fabricate a device with a structure that is the reverse of the one illustrated in FIG. 1 by piling the cathode 7, the electron-transporting layer 6, the light-emitting layer 5, the hole-transporting layer 4, and the anode 2 one upon another in this order on the substrate 1 and, as described earlier, it is possible to dispose the organic EL device of this invention between two substrates at least one of which is highly transparent. In this case of the reverse structure, a layer or layers may be added or omitted as needed.

The organic EL device of this invention is applicable to a single device, a device with its structure arranged in array, or a device in which the anode and the cathode are arranged in X-Y matrix. This invention provides an organic EL device which is enhanced in luminous efficiency and markedly improved in driving stability compared with the conventional devices utilizing emission of light from the excited singlet state by incorporating the aforementioned compound for organic EL device together with a phosphorescent dopant in the light-emitting layer and the device can perform excellently in applications to full-color or multicolor panels.

EXAMPLES

This invention will be explained in more detail below with reference to the examples; however, this invention will not be limited to these examples and it can be reduced to practice in various modes unless such practice exceeds the substance of this invention.

The synthesis of compounds for organic EL device was carried out according to the routes described below. The compound number corresponds to the number assigned to the chemical formula illustrated earlier.

Example 1

Synthesis of Compound 1

In a 2,000-mL three-necked flask were placed 20 g (143 millimoles) of 2-fluorophenylboronic acid, 14 g (59 millimoles) of 1,3-dibromobenzene, and tetrakis(triphenylphosphine)palladium(0), then 300 mL of ethanol and 600 mL of toluene were added, and the mixture was stirred. Thereafter, a solution of 76 g (710 millimoles) of sodium carbonate in 400 mL of water was thrown into the flask. Then, the mixture was heated to 80° C. and stirred for 4 hours. The reaction solution was cooled to room temperature, transferred to a 2,000-mL separatory funnel, and separated into an organic layer and an aqueous layer. The organic layer was washed three times with 200 mL of water and then dehydrated over magnesium sulfate, the magnesium sulfate was filtered off, and the solvent was distilled off under reduced pressure. The reaction mixture thus obtained was purified by silica gel column chromatography to yield 14 g of Intermediate (I) as a colorless transparent liquid.

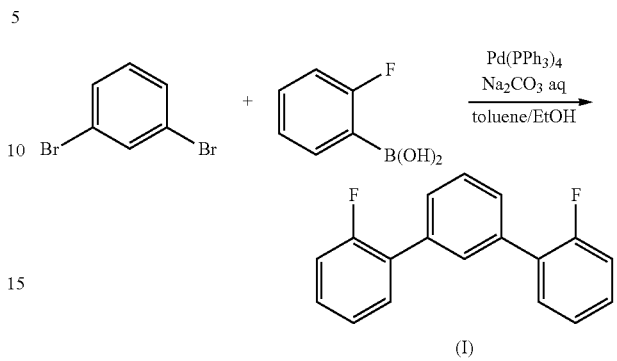

In a 300-mL three-necked flask were placed 6.5 g (149 millimoles) of sodium hydride (55% dispersion) and 90 mL of anhydrous DMF and stirred under nitrogen flow. To the resulting suspension was added a solution of 20 g (122 millimoles) of carbazole in 30 mL of DMF. The mixture was stirred at room temperature for 20 minutes, a solution of 14 g of Intermediate (I) in 30 mL of DMF was added, and the resulting mixture was heated at 120° C. with stirring for 10 days. The mixture was then cooled to room temperature, 50 mL of methanol and 200 mL of water were added, and the solid separated was collected by filtration. The solid was washed by dispersion in methanol with application of heat, then purified by crystallization from THF and methanol, and further purified by crystallization from methylene chloride and ethanol. The white solid obtained was dried by heating under reduced pressure to yield 13 g of Compound 1: EI-MS, 561 (M+1); melting point, 248° C.; glass transition temperature, 91° C.

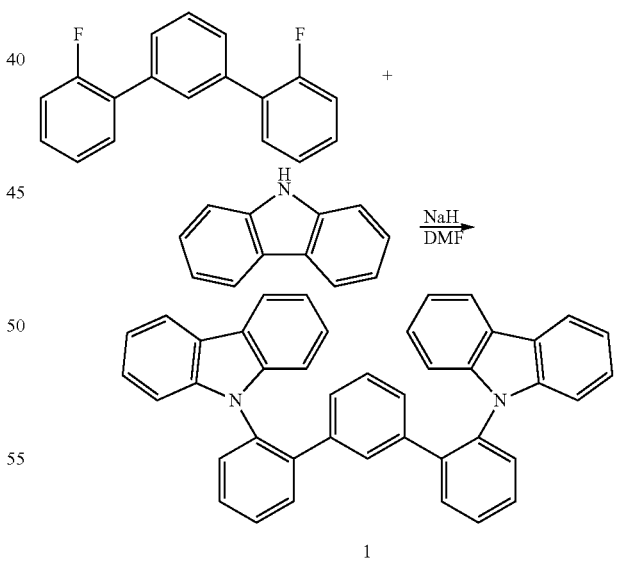

Example 2

Synthesis of Compound 2

In a 2,000-mL three-necked flask were placed 20 g (143 millimoles) of 2-fluorophenylboronic acid, 14 g (59 millimoles) of 2,6-dibromopyridine, and tetrakis(triphenylphosphine)palladium(0), then 300 mL of ethanol and 600 mL of toluene were added, and the mixture was stirred. Thereafter, a solution of 76 g (710 millimoles) of sodium carbonate in 400 mL of water was thrown into the flask. Then, the mixture was heated to 80° C. and stirred for 4 hours. The reaction solution was cooled to room temperature, transferred to a 2,000-mL separatory funnel, and separated into an organic layer and an aqueous layer. The organic layer was washed three times with 200 mL of water and then dehydrated over magnesium sulfate, the magnesium sulfate was filtered off, and the solvent was distilled off under reduced pressure. The reaction mixture thus obtained was purified by silica gel column chromatography to yield 9.8 g of Intermediate (II) as a white solid.

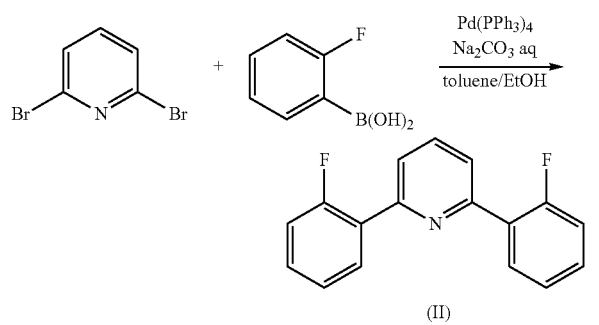

In a 300-mL three-necked flask were placed 4.3 g (99 millimoles) of sodium hydride (55% dispersion) and 60 mL of anhydrous DMF and stirred under nitrogen flow. To the resulting suspension was added a solution of 11 g (66 millimoles) of carbazole in 20 mL of DMF. The mixture was stirred at room temperature for 20 minutes, a solution of 8 g of Intermediate (II) in 20 mL of DMF was added, and the resulting mixture was heated at 120° C. with stirring for 4 days. The mixture was then cooled to room temperature, 40 mL of methanol and 180 mL of water were added, and the solid separated was collected by filtration. The solid was washed by dispersion in methanol with application of heat and then purified by crystallization from THF and methanol. The white solid obtained was dried by heating under reduced pressure to yield 7.6 g of Compound 2: ELMS, 562 (M+1); melting point, 279° C.; glass transition temperature, 94° C.

Example 3

Synthesis of Compound 16

In a 2,000-mL three-necked flask were placed 20 g (143 millimoles) of 2-fluorophenylboronic acid, 14 g (59 millimoles) of 1,4-dibromobenzene, and tetrakis(triphenylphosphine)palladium(0), then 300 mL of ethanol and 600 mL of toluene were added, and the mixture was stirred. Thereafter, a solution of 76 g (710 millimoles) of sodium carbonate in 400 mL of water was thrown into the flask. Then, the mixture was heated to 80° C. and stirred for 4 hours. The reaction solution was cooled to room temperature, transferred to a 2,000-mL separatory funnel, and separated into an organic layer and an aqueous layer. The organic layer was washed three times with 200 mL of water and then dehydrated over magnesium sulfate, the magnesium sulfate was filtered off, and the solvent was distilled off under reduced pressure. The reaction mixture thus obtained was purified by silica gel column chromatography to yield 7 g of Intermediate (III) as a white solid.

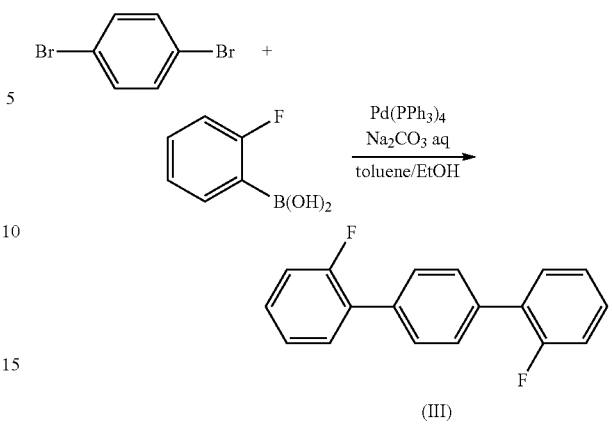

In a 200-mL three-necked flask were placed 3.5 g (80 millimoles) of sodium hydride (55% dispersion) and 60 mL of anhydrous DMF and stirred under nitrogen flow. To the resulting suspension was added a solution of 11 g (66 millimoles) of carbazole in 30 mL of DMF. The mixture was stirred at room temperature for 20 minutes, a solution of 7 g of Intermediate (III) in 15 mL of DMF was added, and the resulting mixture was heated at 120° C. with stirring for 13 days. The mixture was then cooled to room temperature, 50 mL of methanol and 200 mL of water were added, and the solid separated was collected by filtration. The solid was washed by dispersion in methanol with application of heat, purified by crystallization from THF and methanol, and further purified by crystallization from methylene chloride and ethanol. The white solid obtained was dried by heating under reduced pressure to yield 5 g of Compound 16: EI-MS, 561 (M+1); melting point, 305° C.; glass transition temperature, not observed.

Example 4

Synthesis of Compound 7

In a 2,000-mL three-necked flask were placed 31.24 g (155.6 millimoles) of 3-bromophenylboronic acid, 25.75 g (78 millimoles) of 1,3-diiodobenzene, and 10.24 g (8.9 millimoles) of tetrakis(triphenylphosphine)palladium(0), then 300 mL of ethanol and 600 mL of toluene were added, and the mixture was stirred. Thereafter, a solution of 76 g (710 millimoles) of sodium carbonate in 400 mL of water was thrown into the flask. Then, the mixture was heated to 80° C. and stirred for 4 hours. The reaction solution was cooled to room temperature, transferred to a 2,000-mL separatory funnel, and separated into an organic layer and an aqueous layer. The organic layer was washed three times with 200 mL of water and then dehydrated over magnesium sulfate, the magnesium sulfate was filtered off, and the solvent was distilled off under reduced pressure. The reaction mixture thus obtained was purified by silica gel column chromatography to yield 16.96 g of Intermediate (IV) as a colorless transparent liquid.

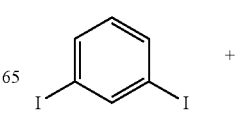

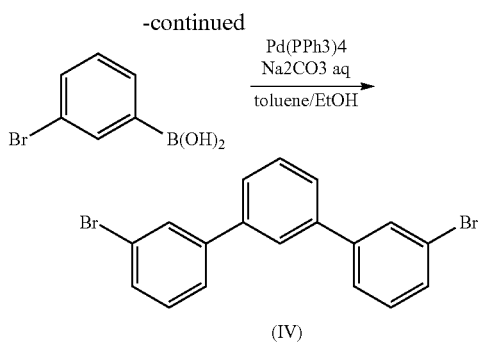

(IV)

In a 1,000-mL three-necked flask were placed 14.25 g (101.84 millimoles) of 2-fluorophenylboronic acid, 15.66 g (40.35 millimoles) of Intermediate (IV), and 3.62 g (3.1 millimoles) of tetrakis(triphenylphosphine)palladium(0), then 100 mL of ethanol and 300 mL of toluene were added, and the mixture was stirred. Thereafter, a solution of 31.6 g (298.1 millimoles) of sodium carbonate in 130 mL of water was thrown into the flask. The mixture was then heated to 80° C. and stirred for 4 hours. The reaction solution was cooled to room temperature, transferred to a 1,000-mL separatory funnel, and separated into an organic layer and an aqueous layer. The organic layer was washed three times with 200 mL of water and then dehydrated over magnesium sulfate, the magnesium sulfate was filtered off, and the solvent was distilled off under reduced pressure. The reaction mixture thus obtained was purified by silica gel column chromatography to yield 9.00 g of Intermediate (V) as a white solid.

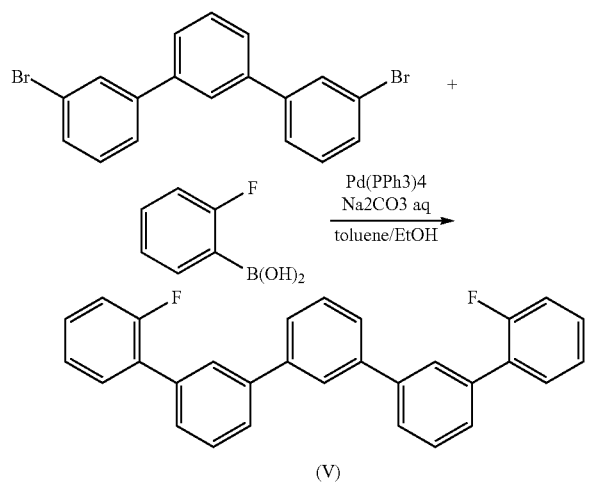

(V)

In a 500-mL three-necked flask were placed 4.22 g (103 millimoles) of sodium hydride (58.8% dispersion) and 100 mL of anhydrous DMF and stirred under nitrogen flow. To the resulting suspension was added a solution of 8.65 g (51.7 millimoles) of carbazole in 30 mL of DMF. The mixture was stirred at room temperature for 30 minutes, a solution of 8.46 g of Intermediate (V) in 70 mL of DMF was added, and the resulting mixture was heated at 120° C. with stirring for 10 days. The mixture was then cooled to room temperature, 50 mL of methanol and 200 mL of water were added, and the solid separated was collected by filtration. The solid was washed by dispersion in methanol with application of heat, purified by crystallization from THF and methanol, and further purified by crystallization from methylene chloride and ethanol. The white solid obtained was dried by heating under reduced pressure and purified by silica gel column chromatography to yield 3.51 g (4.92 millimoles) of Compound 7: EI-MS, 713 (M+1); melting point, 203° C.; glass transition temperature, 98° C.

Example 5

Synthesis of Compound 11

In a 1,000-mL three-necked flask were placed 11.0 g (38.3 millimoles) of 2-carbazolylphenylboronic acid, 6.0 g (15.0 millimoles) of 3,6-dibromo-9-phenylcarbazole, and 1.6 g (1.4 millimoles) of tetrakis(triphenylphosphine)palladium (0), then 100 mL of ethanol and 200 mL of toluene were added, and the mixture was stirred. Thereafter, a solution of 15.0 g (142.0 millimoles) of sodium carbonate in 200 mL of water was thrown into the flask. The mixture was then heated to 80° C. and stirred for 15 hours. The reaction solution was cooled to room temperature, transferred to a 1,000-mL separatory funnel, and separated into an organic layer and an aqueous layer. The organic layer was washed three times with 200 mL of water and then dehydrated over magnesium sulfate, the magnesium sulfate was filtered off, and the solvent was distilled off under reduced pressure. The reaction mixture thus obtained was purified by recrystallization from THF and methanol to yield 5.1 g of Compound 11 as a white solid; EI-MS, 726 (M+1); melting point, 275° C.; glass transition temperature, 143° C.

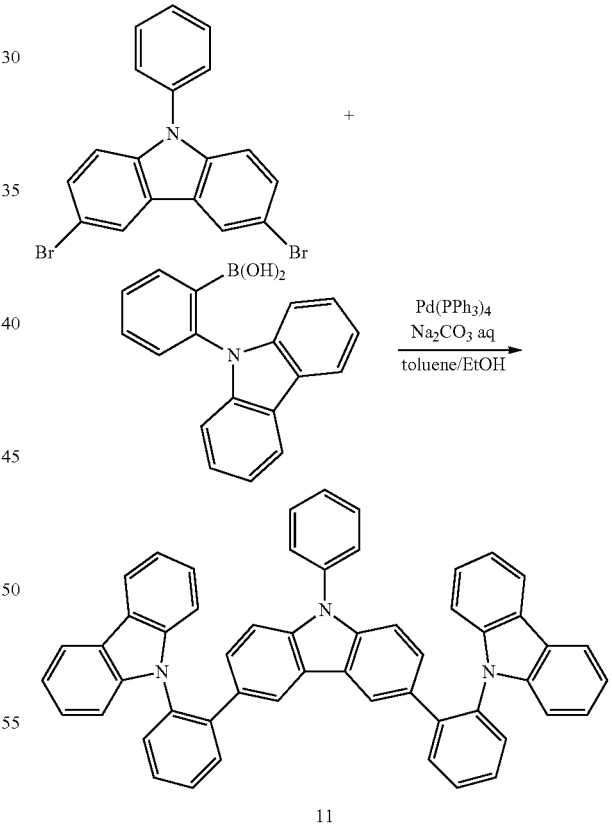

11

Example 6

Synthesis of Compound 12

In a 1,000-mL three-necked flask were placed 8.0 g (27.8 millimoles) of 2-carbazolylphenylboronic acid, 4.0 g (12.8 millimoles) of Intermediate (VI), and 1.6 g (1.4 millimoles) of tetrakis(triphenylphosphine)palladium(0), then 75 mL of ethanol and 150 mL of toluene were added, and the mixture was stirred. Thereafter, a solution of 14.3 g (135.0 millimoles) of sodium carbonate in 150 mL of water was thrown into the flask. The mixture was then heated to 80° C. and stirred for 17 hours. The reaction solution was cooled to room temperature, transferred to a 1,000-mL separatory funnel, and separated into an organic layer and an aqueous layer. The organic layer was washed three times with 200 mL of water and then dehydrated over magnesium sulfate, the magnesium sulfate was filtered off, and the solvent was distilled off under reduced pressure. The reaction mixture thus obtained was purified by recrystallization from THF and methanol to yield 5.1 g of Compound 12 as a white solid; EI-MS, 637 (M+1); melting point, 235° C.; glass transition temperature, 98° C.

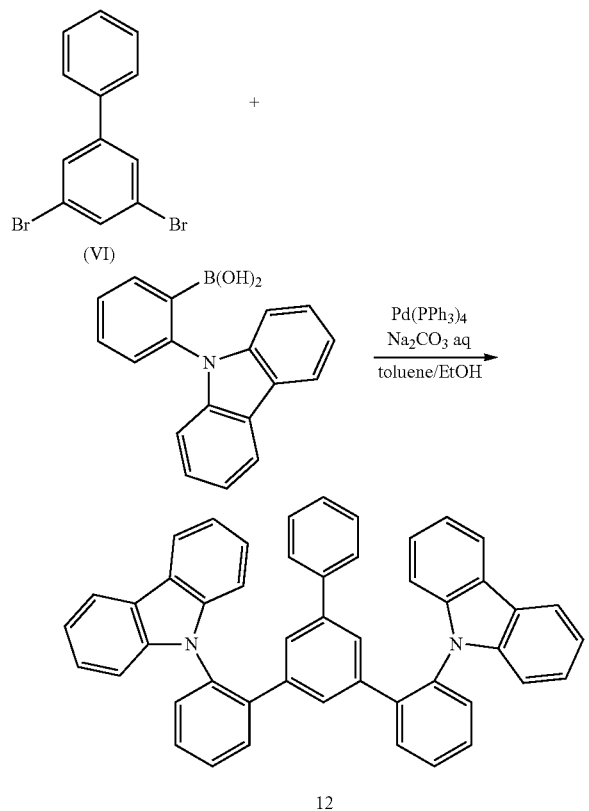

12

Example 7

Synthesis of Compound 24

In a 1,000-mL three-necked flask were placed 8.0 g (27.8 millimoles) of 2-carbazolylphenylboronic acid, 4.0 g (12.8 millimoles) of 1,3-dibromo-5-fluorobenzene, and 1.6 g (1.4 millimoles) of tetrakis(triphenylphosphine)palladium(0), then 75 mL of ethanol and 150 mL of toluene were added, and the mixture was stirred. Thereafter, a solution of 14.3 g (135.0 millimoles) of sodium carbonate in 150 mL of water was thrown into the flask. The mixture was then heated to 80° C. and stirred for 17 hours. The reaction solution was cooled to room temperature, transferred to a 1,000-mL separatory funnel, and separated into an organic layer and an aqueous layer. The organic layer was washed three times with 200 mL of water and then dehydrated over magnesium sulfate, the magnesium sulfate was filtered off, and the solvent was distilled off under reduced pressure. The reaction mixture thus obtained was purified by recrystallization from THF and methanol to yield 5.1 g of Compound 24 as a white solid; EI-MS, 579 (M+1); melting point, 279° C.; glass transition temperature, 86° C.

Example 8

Synthesis of Compound 27

In a 1,000-mL three-necked flask were placed 25.4 g (84.0 millimoles) of 2-carbazolylphenylboronic acid, 12.5 g (40.0 millimoles) of 3,3'-dibromobiphenyl, and 0.8 g (0.7 millimole) of tetrakis(triphenylphosphine)palladium(0), then 40 mL of ethanol and 80 mL of toluene were added, and the mixture was stirred. Thereafter, a solution of 14.3 g (135.0 millimoles) of sodium carbonate in 150 mL of water was thrown into the flask. The mixture was then heated to 80° C. and stirred for 17 hours. The reaction solution was cooled to room temperature, transferred to a 1,000-mL separatory funnel, and separated into an organic layer and an aqueous layer. The organic layer was washed three times with 200 mL of water and then dehydrated over magnesium sulfate, the magnesium sulfate was filtered off, and the solvent was distilled off under reduced pressure. The reaction mixture thus obtained was purified by silica gel column chromatography to yield 5.0 g of Compound 27 as a white solid; EI-MS, 637 (M+1); melting point, not observed; glass transition temperature, 96° C.

Example 9

Synthesis of Compound 31

In a 1,000-mL three-necked flask were placed 8.0 g (27.8 millimoles) of 2-carbazolylphenylboronic acid, 4.0 g (12.8 millimoles) of 1,4-dibromo-2,5-difluorobenzene, and 1.6 g (1.4 millimoles) of tetrakis(triphenylphosphine)palladium(0), then 75 mL of ethanol and 150 mL of toluene were added, and the mixture was stirred. Thereafter, a solution of 14.3 g (135.0 millimoles) of sodium carbonate in 150 mL of water was thrown into the flask. The mixture was then heated to 80° C. and stirred for 17 hours. The reaction solution was cooled to room temperature, transferred to a 1,000-mL separatory funnel, and separated into an organic layer and an aqueous layer. The organic layer was washed three times with 200 mL of water and then dehydrated over magnesium sulfate, the magnesium sulfate was filtered off, and the solvent was distilled off under reduced pressure. The reaction mixture thus obtained was purified by recrystallization from THF and methanol to yield 5.1 g of Compound 31 as a white solid; EI-MS, 597 (M+1); melting point, 263° C.; glass transition temperature, 92° C.

Example 10

Synthesis of Compound 32

In a 2,000-mL three-necked flask were placed 19.0 g (60.0 millimoles) of 1,3,5-tribromobenzene, 36.0 g (125 millimoles) of 2-carbazolylphenylboronic acid, and 1.6 g (1.4 millimoles) of tetrakis(triphenylphosphine)palladium(0), then 100 mL of ethanol and 600 mL of toluene were added, and the mixture was stirred. Thereafter, a solution of 50.0 g (471.0 millimoles) of sodium carbonate in 480 mL of water was thrown into the flask. The mixture was then heated to 80° C. and stirred for 24 hours. The reaction solution was cooled to room temperature, transferred to a 2,000-mL separatory funnel, and separated into an organic layer and an aqueous layer. The organic layer was washed three times with 200 mL of water and then dehydrated over magnesium sulfate, the magnesium sulfate was filtered off, and the solvent was distilled off under reduced pressure. The reaction mixture thus obtained was purified by silica gel column chromatography to yield 17.2 g of Intermediate (VII) as a white solid.

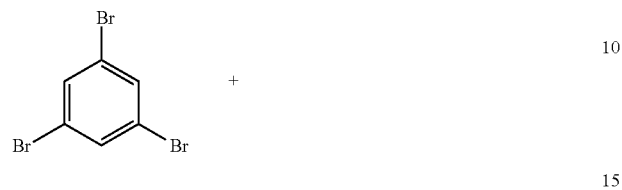

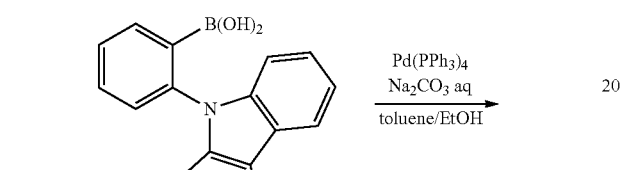

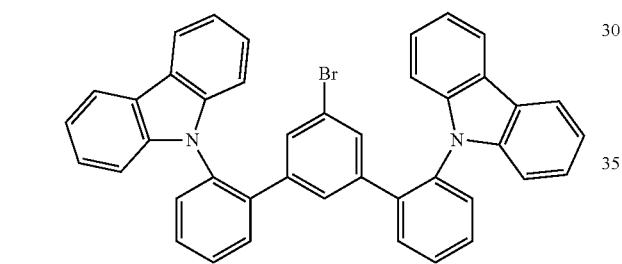

In a 1,000-mL three-necked flask were placed 2.6 g (16.2 millimoles) of 3,5-difluorophenylboronic acid, 8.0 g (12.5 millimoles) of Intermediate (VII), and 0.8 g (0.7 millimole) of tetrakis(triphenylphosphine)palladium(0), then 60 mL of ethanol and 120 mL of toluene were added, and the mixture was stirred. Thereafter, a solution of 5.9 g (135.0 millimoles) of sodium carbonate in 48 mL of water was thrown into the flask. The mixture was then heated to 80° C. and stirred for 17 hours. The reaction solution was cooled to room temperature, transferred to a 1,000-mL separatory funnel, and separated into an organic layer and an aqueous layer. The organic layer was washed three times with 200 mL of water and then dehydrated over magnesium sulfate, the magnesium sulfate was filtered off, and the solvent was distilled off under reduced pressure. The reaction mixture thus obtained was purified by recrystallization from THF and methanol to yield 5.6 g of Compound 32 as a white solid; ELMS, 673 (M+1); melting point, 217° C.; glass transition temperature, 92° C.

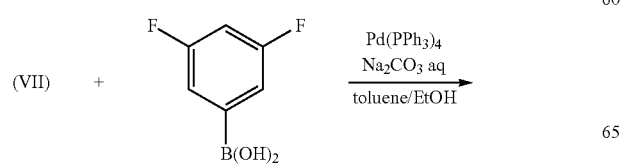

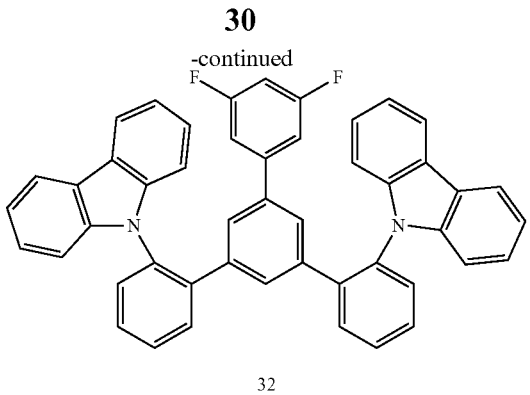

32

Example 11

Synthesis of Compound 33

In a 1,000-mL three-necked flask were placed 4.7 g (18.0 millimoles) of 3,5-ditrifluoromethylphenylboronic acid, 9.0 g (14.0 millimoles) of Intermediate (VII), and 0.8 g (0.7 millimole) of tetrakis(triphenylphosphine)palladium(0), then 60 mL of ethanol and 120 mL of toluene were added, and the mixture was stirred. Thereafter, a solution of 5.9 g (135.0 millimoles) of sodium carbonate in 48 mL of water was thrown into the flask. The mixture was then heated to 80° C. and stirred for 17 hours. The reaction solution was cooled to room temperature, transferred to a 1,000-mL separatory funnel, and separated into an organic layer and an aqueous layer. The organic layer was washed three times with 200 mL of water and then dehydrated over magnesium sulfate, the magnesium sulfate was filtered off, and the solvent was distilled off under reduced pressure. The reaction mixture thus obtained was purified by recrystallization from THF and methanol to yield 7.1 g of Compound 33 as a white solid; ELMS, 772 (M+1); melting point, 178° C.; glass transition temperature, 80° C.

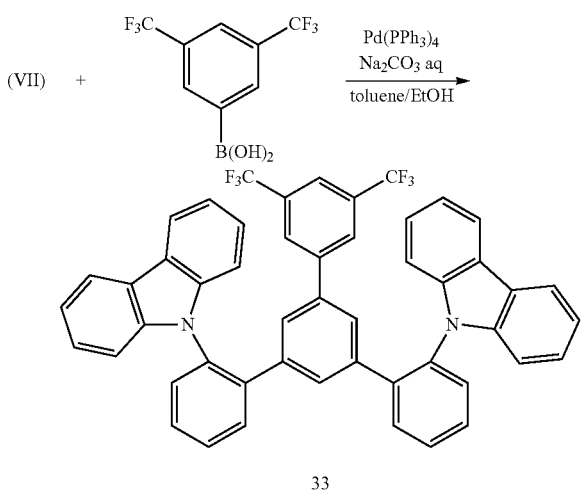

33

Example 12

Applying the vacuum deposition process at a degree of vacuum of $4.0 \times 10^{-4}$ Pa, the constituent layers in thin film were piled one upon another on a glass substrate on which a 110 nm-thick indium tin oxide (ITO) anode had been formed.

First, copper phthalocyanine (CuPC) was deposited on the ITO anode to a thickness of 30 nm as a hole-injecting layer. Then, NPB was deposited to a thickness of 80 nm as a hole-transporting layer. Next, a light-emitting layer was formed by co-depositing from different evaporation sources Compound 1 as a host material and iridium(III) bis[(4,6-difluorophenyl)pyridinato-N,C2']picolinate (FIrpic), which is a blue-emitting iridium complex, as a dopant to a thickness of 35 nm. The concentration of FIrpic was 8.0 wt %. Then, Alq3 was deposited to a thickness of 25 nm as an electron-transporting layer. Further, lithium fluoride (LiF) was deposited on the electron-transporting layer to a thickness of 0.5 nm as an electron-injecting layer. Finally, aluminum (Al) as an electrode was deposited on the electron-injecting layer to a thickness of 170 nm to complete the fabrication of an organic EL device which has the structure illustrated in FIG. 1 with an electron-injecting layer added between a cathode and an electron-transporting layer.

The organic EL device thus fabricated was connected to an outside power source and, upon application of direct current voltage, the device emitted light with the luminous characteristics shown in Table 1. In Table 1, the luminance, voltage, and luminous efficiency are measured at 10 mA/cm². The maximum wavelength of the spectrum of light emitted from the device is 470 nm and this proves that light is emitted from FIrpic.

Example 13

An organic EL device was fabricated as in Example 12 with the exception of using Compound 2 as the host material in the light-emitting layer.

Example 14

An organic EL device was fabricated as in Example 12 with the exception of using Compound 16 as the host material in the light-emitting layer.

Example 15

An organic EL device was fabricated as in Example 12 with the exception of using Compound 7 as the host material in the light-emitting layer.

Example 16

An organic EL device was fabricated as in Example 12 with the exception of using Compound 11 as the host material in the light-emitting layer.

Example 17

An organic EL device was fabricated as in Example 12 with the exception of using Compound 12 as the host material in the light-emitting layer.

Example 18

An organic EL device was fabricated as in Example 12 with the exception of using Compound 24 as the host material in the light-emitting layer.

Example 19

An organic EL device was fabricated as in Example 12 with the exception of using Compound 27 as the host material in the light-emitting layer.

Example 20

An organic EL device was fabricated as in Example 12 with the exception of using Compound 31 as the host material in the light-emitting layer.

Example 21

An organic EL device was fabricated as in Example 12 with the exception of using Compound 32 as the host material in the light-emitting layer.

Example 22

An organic EL device was fabricated as in Example 12 with the exception of using Compound 33 as the host material in the light-emitting layer.

Comparative Example 1

An organic EL device was fabricated as in Example 12 with the exception of using mCP as the host material in the light-emitting layer.

Comparative Example 2

An organic EL device was fabricated as in Example 12 with the exception of using 2,2'-bis(N-carbazolyl)biphenyl described in patent document 3 as the host material in the light-emitting layer.

The luminous characteristics measured in the examples and comparative examples are shown in Table 1. In each of the organic EL devices fabricated in Examples 12 to 22 and Comparative Examples 1 and 2, the maximum wavelength of the light emitted from the device was 470 nm and the light was identified to be emitted from FIrpic

TABLE 1

|  | Luminance (cd/m²) (@ 2.5 mA/cm²) | Voltage (@ 2.5 mA/cm²) | Luminous efficiency (@ 2.5 mA/cm²) | Driving life (@ 7.5 mA/cm²) |
| --- | --- | --- | --- | --- |
| Example12 | 437 | 11 | 4.2 | 343 |
| Example13 | 341 | 11 | 4.2 | 290 |
| Example14 | 292 | 10 | 3.9 | 235 |
| Example15 | 340 | 10 | 4.2 | 453 |
| Example16 | 316 | 11 | 1.4 | 326 |
| Example17 | 263 | 11 | 3.1 | 380 |
| Example18 | 292 | 11 | 3.1 | 253 |
| Example19 | 342 | 11 | 3.9 | 291 |
| Example20 | 296 | 10 | 3.5 | 235 |
| Example21 | 371 | 10 | 2.9 | 199 |

TABLE 1-continued

| | Luminance (cd/m$^2$) (@ 2.5 mA/cm$^2$) | Voltage (@ 2.5 mA/cm$^2$) | Luminous efficiency (@ 2.5 mA/cm$^2$) | Driving life (@ 7.5 mA/cm$^2$) |
|---|---|---|---|---|
| Example22 | 398 | 10 | 4.0 | 235 |
| Comparative example1 | 243 | 11 | 2.8 | 181 |
| Comparative example2 | 24 | 11 | 0.2 | 109 |

INDUSTRIAL APPLICABILITY

The compound for organic EL device of this invention has a marked ability to inject and transport electrical charges and lowers the driving stability when used in an organic EL device. Further, the electrical charges become well balanced in the light-emitting layer and this improves the probability of their recombination. Still further, as the lowest triplet energy of the compound is sufficiently high to confine the lowest triplet energy of the dopant, the compound can effectively suppress the transfer of the triplet energy from the dopant to the host molecule. These properties are responsible for attaining high luminous efficiency. In addition, the compound shows good properties in the amorphous state, high heat resistance, and good electrochemical stability and has contributed to realize an organic EL device of long driving life and good durability.

The organic EL device of this invention is at a level for practical use in respect to luminous characteristics, driving life, and durability and is of high technical value in applications to flat panel displays (mobile phone display devices, vehicle-mounted display devices, office computer display devices, television sets, and the like), light sources utilizing the characteristics of planar light emitters (illumination, light sources for copiers, and backlight sources for liquid crystal displays and instruments), signboards, and beacon lights.

The invention claimed is:

1. An organic electroluminescent device comprising an anode, organic layers, and a cathode piled one upon an on a substrate, wherein said organic layers comprise a light-emitting layer comprising a compound for organic electroluminescent device represented by general formula (1) and a phosphorescent dopant:

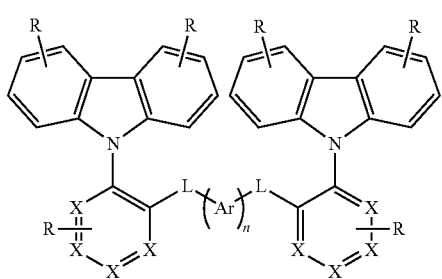

(1)

wherein Ar is a divalent aromatic hydrocarbon group of 6 carbon atoms optionally containing substituents and the substituents are selected from the group consisting of a phenyl group, and an alkyl group of 1-4 carbon atoms;
L is a direct bond;
X is a methine group;
R is a hydrogen atom; and
n is an integer of 1;
wherein in the case where L is a direct bond, not all of the bonds between L and Ar are located at the adjacent position in the aromatic rings constituting Ar.

2. An organic electroluminescent device as described in claim 1, wherein the compound for organic electroluminescent device is a compound represented by general formula (2):

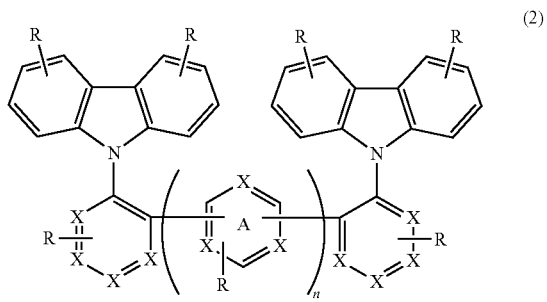

(2)

wherein n, X, and R respectively have the same meanings as in general formula (1), with the proviso that R bonded to ring A is a hydrogen atom, a phenyl group, or an alkyl group of 1-4 carbon atoms; and two bonds linking the adjacent rings are not located at the ortho position of ring.

3. An organic electroluminescent device as described in claim 1, wherein the compound for organic electroluminescent device is a compound selected from the group consisting of the following compounds:

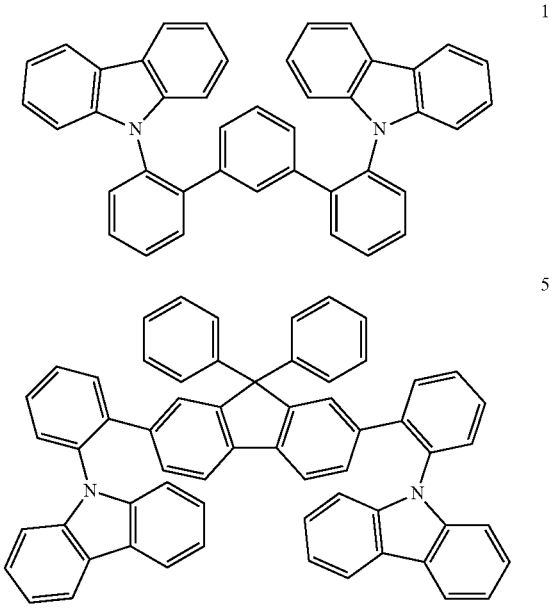

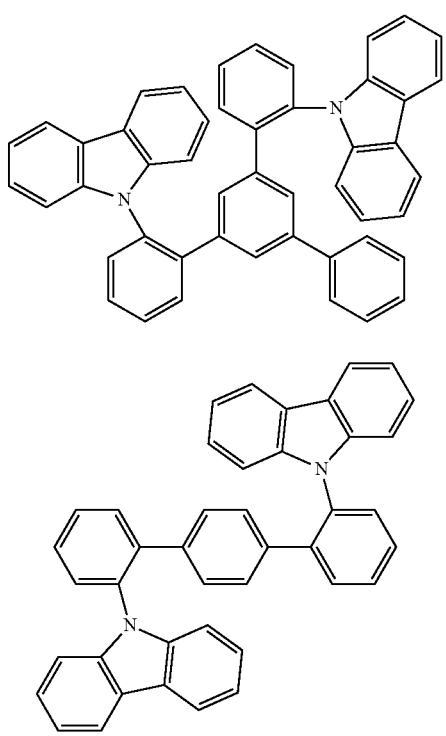
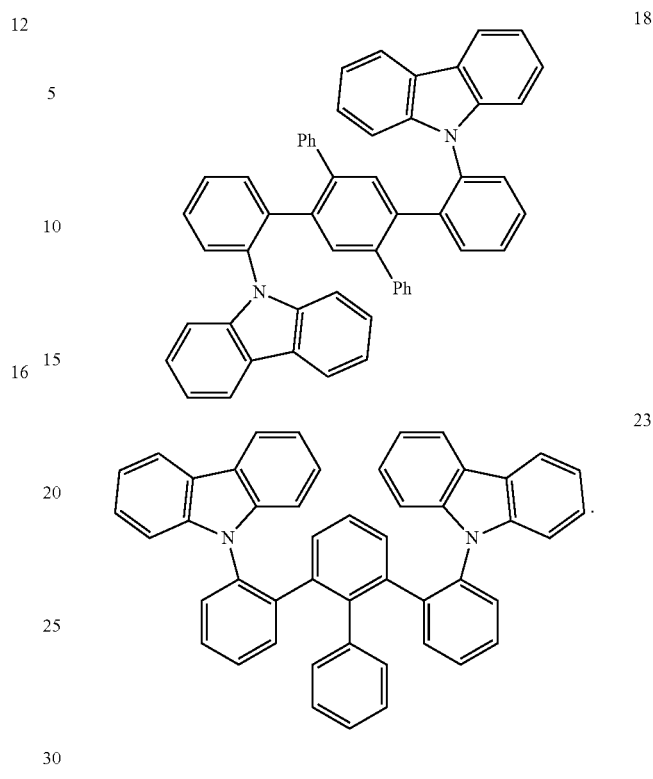
* * * * *